United States Patent
Tan (10) Patent No.: US 7,708,774 B1
(45) Date of Patent: *May 4, 2010

(54) POLYETHYLENE OXIDE AND SILICONE COPOLYMERS AND THEIR USAGE ON MEDICAL DEVICES

(75) Inventor: Jiahong Tan, Canyon Country, CA (US)

(73) Assignee: Pacesetter, Inc., Sylmar, CA (US)

( * ) Notice: Subject to any disclaimer, the term of this patent is extended or adjusted under 35 U.S.C. 154(b) by 565 days.

This patent is subject to a terminal disclaimer.

(21) Appl. No.: 11/563,593

(22) Filed: Nov. 27, 2006

Related U.S. Application Data (63) Continuation-in-part of application No. 11/281,778, filed on Nov. 16, 2005, now abandoned, and a continuation-in-part of application No. 11/281,297, filed on Nov. 16, 2005, now Pat. No. 7,553,546.

(51) Int. Cl.
*B32B 9/04* (2006.01)

(52) U.S. Cl. .................. 623/1.46; 428/447; 525/452; 525/453; 525/474; 525/477; 528/25; 528/28; 623/23.59

(58) Field of Classification Search .................. None
See application file for complete search history.

(56) References Cited

U.S. PATENT DOCUMENTS

| | | | |
|---|---|---|---|
| 3,480,583 A * | 11/1969 | O'Connor et al. ......... 556/446 |
| 4,276,394 A | 6/1981 | Kennedy et al. |
| 4,316,973 A | 2/1982 | Kennedy |
| 4,342,849 A | 8/1982 | Kennedy |
| 4,861,830 A | 8/1989 | Ward, Jr. |
| 4,872,867 A | 10/1989 | Joh |
| 4,888,389 A | 12/1989 | Kennedy et al. |
| 4,910,321 A | 3/1990 | Kennedy et al. |
| 5,240,970 A * | 8/1993 | Nichols et al. ............. 521/128 |
| 5,240,971 A | 8/1993 | Eckberg |
| 5,277,753 A | 1/1994 | Kelley et al. |
| 5,358,516 A | 10/1994 | Myers et al. |
| 5,629,133 A | 5/1997 | Wolf et al. |
| 5,686,499 A * | 11/1997 | Fishback ............. 521/112 |
| 5,840,083 A | 11/1998 | Braach-Maksvytis |
| 5,843,149 A | 12/1998 | Ebert et al. |
| 5,902,329 A | 5/1999 | Hoffmann et al. |
| 6,046,143 A | 4/2000 | Khan et al. |
| 6,200,589 B1 | 3/2001 | Kennedy et al. |
| 6,310,169 B1 * | 10/2001 | Kawabata et al. ............ 528/28 |
| 6,365,171 B1 | 4/2002 | Kennedy et al. |
| 6,521,736 B2 | 2/2003 | Watterson et al. |
| 6,555,619 B1 | 4/2003 | Kennedy et al. |
| 6,567,704 B2 | 5/2003 | Sundquist et al. |
| 6,723,814 B2 | 4/2004 | Meier et al. |
| 6,936,298 B2 | 8/2005 | Chaikof et al. |
| 7,211,108 B2 | 5/2007 | Furst et al. |
| 7,553,546 B1 | 6/2009 | Tan |
| 2002/0123087 A1 | 9/2002 | Vachon et al. |
| 2003/0028224 A1 | 2/2003 | McVenes et al. |
| 2003/0204022 A1 | 10/2003 | Kennedy et al. |
| 2005/0004661 A1 | 1/2005 | Lewis et al. |
| 2005/0060015 A1 | 3/2005 | Tanaka |
| 2005/0147647 A1 | 7/2005 | Glauser et al. |
| 2005/0282997 A1 | 12/2005 | Ward et al. |
| 2007/0226917 A1 | 10/2007 | Kleen et al. |
| 2008/0311173 A1 | 12/2008 | Schwarz et al. |

FOREIGN PATENT DOCUMENTS

| | | |
|---|---|---|
| EP | 1314449 A2 | 5/2003 |
| EP | 1314449 A3 | 5/2003 |
| WO | 0202674 A1 | 1/2002 |
| WO | 2004044012 A1 | 5/2004 |
| WO | 2004052324 A1 | 6/2004 |
| WO | WO 2005/102253 A1 * | 11/2005 |

OTHER PUBLICATIONS

NonFinal Office Action, mailed Oct. 3, 2007: Related U.S. Appl. No. 11/281,297.
Erdodi, Gabor et al., "Novel Amphiphilic Conetworks Composed of Poly(Ethylene Glycol) and Polyisobutylene Chain Segments," Polym. Mater. Sci. Eng. 1998; 79:481-482.
Freij-Larsson, Christina et al., "Polyurethane surfaces modified by amphiphilic polymers: effects of protein adsorption," Biomaterials 2000; 21:307-315.
Groenewolt, Mattijs., et al., "Polyisobutylene-block-Poly(ethylene oxide) for Robust Templating of Highly Ordered Mesoporous Materials," Adv. Mater. 2005; 17:1158-1162.
Jialanella, Gary L. et al., "Synthesis of Polystyrene-Block-Polyoxyethylene for Use as a Stabilizer in the Emulsion Polymerization of Styrene," J. Polym. Sci., A-Polym. Chem., 1992; 30:1925-1933.

(Continued)

*Primary Examiner*—Marc S Zimmer (57) ABSTRACT

An implantable medical device includes a device body at least partially formed of a polymeric material including a base polymer and a block copolymer. The block copolymer includes at least one polyethylene oxide (PEO) block and at least one silicone (SI) block, wherein the weight average molecular weight of the block copolymer is in the range of about 400 to about 50,000.

3 Claims, 3 Drawing Sheets

OTHER PUBLICATIONS

Lee, Jin Ho et al., "Platelet adhesion onto segmented polyurethane film surfaces modified by addition and crosslinking of PEO-containing block copolymers," Biomaterials 2000; 21:683-691.

Martinez-Castro, N., "New Block Copolymers of Isobutylene by Combination and Anionic Polymerizations," dissertation abstract, obtainable at http://opus.ub.uni-bayreuth.de/volltexte/2005/134/, dated Mar. 9, 2005.

Park, JaeHung et al., "Hydrogels based on poly(ethylene oxide) and poly(tetramethylene oxide) or poly(dimethyl siloxane): synthesis, characterization, in vitro protein adsorption and platelet adhesion," Biomaterials 2002; 23:1797-1808.

Puskas, Judit E. et al., "Polyisobutylene-Based Biomaterials," J. Polym. Sci., A-Polym. Chem., 2004; 42:3091-3109.

Richard, R.E., et al., "Novel Polyisobutylene-based Block Copolymer Technology For the Controlled Release of Paclitaxel From Coronary Stents," Society for Biomaterials, 30th Annual Meeting Transactions, pp. 18-19, (2005).

Rooney, J.M., "Synthesis of a Block Copolymer Containing Polyisobutylene and Polyethlyene Oxide Segments," J. Polym. Sci., Polym. Chem Ed. 1981; 19:2119-2122.

Tan, Jiahong et al., "Surface modification of polyurethanes using PEO-containing copolymers as additives: reduced fibrinogen adsorption correlates with reduced platelet adhesion," Society for Biomaterials 29th Annual Meeting Transactions, p. 470 (2003).

Tan, Jiahong, "Polyethylene oxide-containing block copolymers as surface modification additives in polyurethanes for protein and cell resistance," Abstract of a Thesis, McMaster University (2004).

Wondraczek, R.H., and Kennedy, J.P. "New Telechelic Polymers and Sequential Copolymers by Polyfunctional Initiator-Transfer Agents (Inifers). 11. Synthesis, Extension and Crosslinking of Oxycarbonyl Isocyanate Telechelic Polyisobutylenes," Polymer Bulletin 1981; 4:445-450.

Vairon, J.P. et al., "Amphiphilic, Bi, Tri, and Star Block Copolymers of Styrene and Acrylic Acid Prepared Via Controlled Radical Polymerization and Their Use as Surfactants in Emulsion Polymerization," Universite Pierre & Marie Curie, UNESCO-SA-2001, presentation slides 1-6.

NonFinal Office Action, mailed Feb. 12, 2008: Related U.S. Appl. No. 11/281,297.

NonFinal Office Action, mailed Jul. 28, 2008: Related U.S. Appl. No. 11/281,297.

Notice of Allowance, mailed Apr. 3, 2009: Related U.S. Appl. No. 11/281,297.

NonFinal Office Action, mailed Feb. 6, 2009: Related U.S. Appl. No. 11/563,573.

Notice of Allowance, mailed Jul. 15, 2009: Related U.S. Appl. No. 11/563,573.

NonFinal Office Action, mailed Apr. 2, 2009: Related U.S. Appl. No. 11/281,778.

* cited by examiner

POLYETHYLENE OXIDE AND SILICONE COPOLYMERS AND THEIR USAGE ON MEDICAL DEVICES

CROSS-REFERENCE TO RELATED APPLICATIONS

This application is a continuation-in-part of U.S. Patent Applications: 1) Ser. No. 11/281,778, filed on Nov. 16, 2005 now abandoned; and 2) Ser. No. 11/281,297, now U.S. Pat. No. 7,553,546, filed on Nov. 16, 2005, the entire disclosures of which are incorporated herein by reference. This application shares common subject matter with copending U.S. patent application Ser. No. 11/563,573 filed currently herewith, titled "Polyethylene Oxide and Polyisobutylene Copolymers and their Usage on Medical Devices", which is incorporated herein by reference in its entirety.

FIELD OF THE INVENTION

The present invention relates generally to biocompatible and lubricious coatings, and more particularly, to polyethylene oxide and silicone copolymers and their usage.

BACKGROUND

Many methods and materials have been explored to achieve biocompatibility of implantable medical devices (IMD). Implantable medical devices, as used herein, include any blood-contacting medical device that is implanted in the body, chronically or otherwise, including, but not limited to, blood-contacting surgical tools, implantable cardiac devices, implantable monitors, biological sensors, implantable drug delivery devices, catheters, artificial blood vessels and stents. For IMDs, it is especially desirable that there be minimal friction during implant to facilitate implant dynamics. To this end, IMDs have been coated with materials which increase wet lubricity, thereby reducing procedure time, insertion forces and patient discomfort. Lubricity also reduces tissue irritation and damage and provides greater control and maneuverability of the device during implant. Wet lubricity for hydrophobic surfaces may be achieved using hydrophilic coatings. Such coatings also improve biocompatibility by, for example, reducing protein adsorption and platelet adhesion and other blood interactions, as well as resisting bacterial adhesion.

For example, lead insulation materials have been surface-coated with a UV-cured polyvinylpyrrolidone (PVP) from SurModics, Inc. of East Prairie, Minn., using PHOTOLINK® chemistry coating technique to achieve the benefits of wet lubricity and hydrophilic coatings. This coating technique involves photochemical covalent bonding of the coating molecules to the insulation material substrate and requires several steps, including lead cleaning, PVP solution preparation, plasma treatment, lead coating, photo activation and cleaning. This process is complex and difficult to control and can lead to poor quality coatings.

Lubricious surfaces can also be prepared by chemical grafting techniques using other hydrophilic materials, such as polyethylene oxide (PEO), referred to also as polyethylene glycol (PEG), which can be grafted to the polymer substrate either as end segments or branches to the back bone of the polymer. The existing techniques and materials, however, do not provide effective lubricious surfaces on medical devices formed of materials including silicone rubber or silicone polyurethane copolymer (SPC). Silicone rubber and SPC are common insulation materials used on medical leads.

What are needed, therefore, are new materials to achieve highly lubricious coatings for implantable medical devices, which are particularly useful for preparing lubricious coatings on silicone and SPC leads or other silicone rubber or SPC medical devices. The present invention provides PEO and silicone copolymers to satisfy these and other needs, and provides further related advantages, as will be made apparent by the description of the embodiments that follow.

BRIEF SUMMARY OF THE INVENTION

Block copolymers presented herein include at least one polyethylene oxide (PEO) block and at least one silicone (SI) block. In one embodiment, the weight average molecular weight of the block copolymer is in the range of about 400 to about 50,000.

An implantable medical device is also presented. The device includes a device body at least partially formed of a polymeric material including a base polymer and the PEO/SI block copolymer. The weight average molecular weight of the PEO/SI block copolymer is in the range of about 400 to about 50,000.

Also presented herein are block copolymers that include at least one polyethylene oxide (PEO) block and at least one polyisobutylene (PIB) block, and an implantable medical device which includes a device body at least partially formed of a polymeric material including a base polymer and the PEO/PIB block copolymer.

BRIEF DESCRIPTION OF THE DRAWINGS/FIGURES

The accompanying drawings, which are incorporated herein and form part of the specification, illustrate the present invention and, together with the description, further serve to explain the principles of the invention and to enable a person skilled in the relevant art(s) to make and use the invention. In the drawings, like reference numbers indicate identical or functionally similar elements.

DETAILED DESCRIPTION OF THE INVENTION

The following detailed description of the present invention refers to the accompanying drawings that illustrate exemplary embodiments consistent with this invention. Other embodiments are possible, and modifications may be made to the embodiments within the spirit and scope of the present invention. Therefore, the following detailed description is not meant to limit the invention. Rather, the scope of the invention is defined by the appended claims. Thus, the operation and behavior of the present invention will be described with the understanding that modifications and variations of the embodiments are possible, given the level of detail presented herein.

Surface modification amphiphilic copolymers (SMAC) contain one or more hydrophilic segments and one or more hydrophobic segments. Since hydrophilic segments of an SMAC can provide wet lubricity to a surface, SMACs can be used as to prepare lubricious coatings on medical device bodies formed of hydrophobic base materials. Such hydrophilic segments may include, for example, polyethylene oxide (PEO) (also known as polyethylene glycol (PEG)), poly(vinyl alcohol) (PVA), polyacrylamides (PA), polyvinylpyrrolidone (PVP), and poly(hydroxyethyl methacrylate) (PHEMA). In addition, hydrophobic segments of an SMAC coating interact with a hydrophobic base material to help anchor the SMAC coating to the surface of the medical device. Such hydrophobic segments may include, for example, polypropylene oxide (PPO), polyurethane (PU), polystyrene (PS), polypropylene (PP), polytetrafluoroethylene (PTFE), polytetramethylene oxide (PTMO), polyisobutylene (PIB), and polyalkyl siloxane (PAS). Polyalkyl siloxane includes poly(dialkyl siloxane) such as poly(dimethyl or diethyl siloxane). A polyalkyl siloxane segment is simply referred to herein as a silicone (SI) segment.

Figure 1:
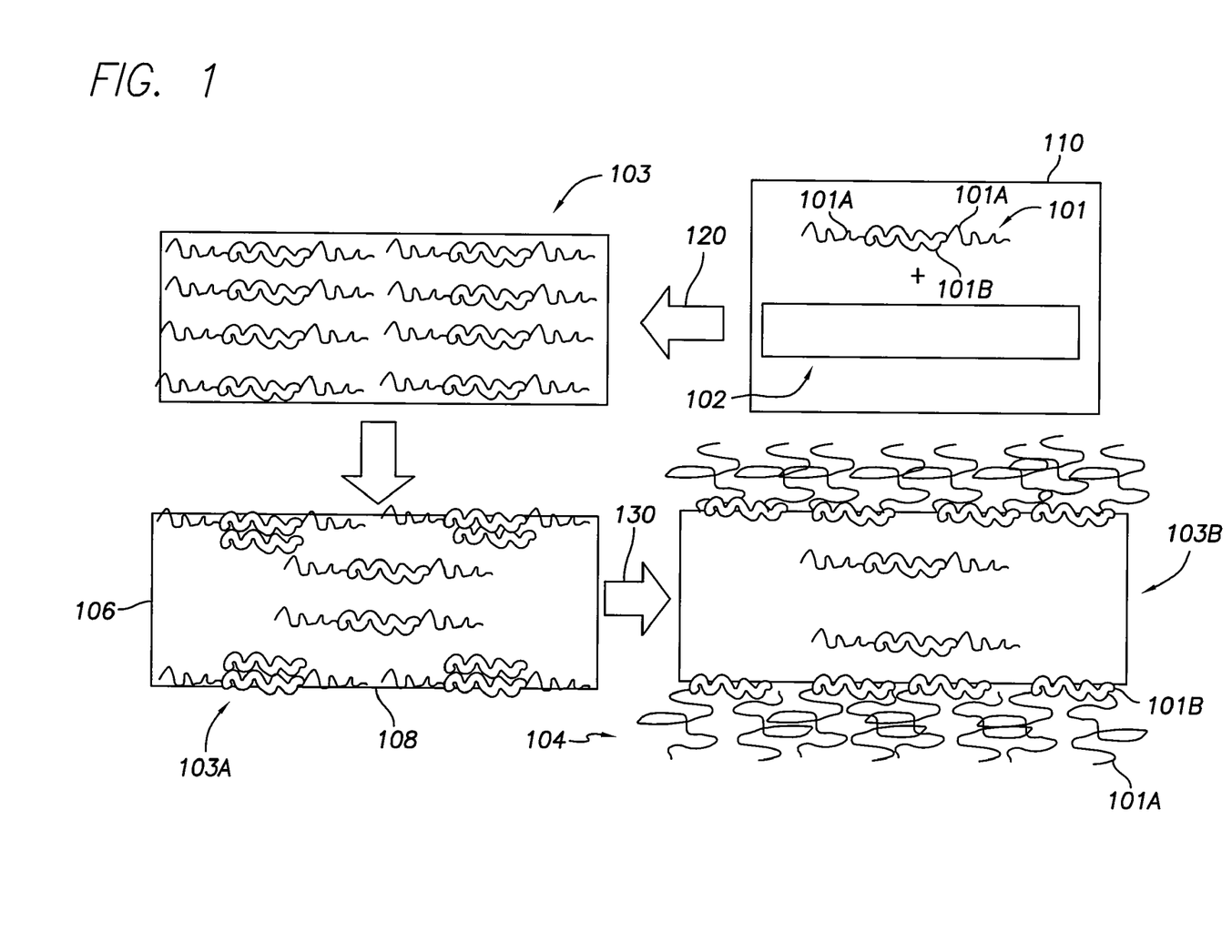
FIG. 1 is a flowchart schematic illustrating a surface modification amphiphilic copolymer (SMAC) blended into a base polymer and forming a lubricious surface coating in accordance with a method disclosed herein.

FIG. 1 shows a surface modification amphiphilic copolymer (SMAC) 101 blended into a base polymer 102 and forming a lubricious coating 104 in accordance with a method disclosed herein. In a blending step 110, SMAC 101 is blended as an additive with a base polymer 102, producing a blended polymeric material. For example, the weight percent of SMAC 101 in the blended polymeric material based on weight of base polymer may be in a range of about 0.2 percent to about 40 percent. In one embodiment, the weight percent of SMAC 101 is about five percent. In any case, the amount of SMAC 101 added to base polymer 102 should be measured so as to achieve a desired wet lubricity and its benefits such as reduction in protein adsorption, bacteria and cell adhesion, and thrombosis formation.

As noted above, SMAC 101 includes at least one hydrophilic segment 101A and at least one hydrophobic segment 101B. The schematic of SMAC 101 in FIG. 1 includes two hydrophilic segments 101A and one hydrophobic segment 101B in the form of an ABA triblock copolymer, but it should be understood that other forms of SMAC 101 are possible, including random block copolymers. For example, SMAC 101 may be a block copolymer in the form of $A(BA)_n$, $(AB)_n$, or $B(AB)_n$, wherein A is one or more hydrophilic segments 101A and B is one or more hydrophobic segments 101B and n is an integer greater than zero. For SMAC 101 in the form of ABA and BAB, the Mw of the SMAC 101 may be in the range of about 400 to about 30,000. In one embodiment, the Mw for the SMAC 101 is in the range of 1,000 to 10,000. Moreover, SMAC 101 may be a random block copolymer, represented generally as a copolymer in the form of "ABBAABABA," wherein each A and B segment may contain many monomer repeat units rather just one monomer repeat unit. It should be understood that other random forms for a random multi-block copolymer are within the scope of the present invention, and "ABBAABABA" as used herein represents any random multi-block copolymer. Moreover, each A segment and each B segment of SMAC 101 need not be identical in kind or segment chain length to any other A segment or B segment, respectively.

In a forming step 120, at least a part 103 of a medical device is formed with the blended polymeric material. As schematically shown by device part 103A, SMAC 101 spontaneously migrates from bulk 106 to surface 108 of device part 103 formed of the blended polymeric material since SMAC 101 is surface active. Step 130 includes implanting the medical device having device part 103 in a patient and allowing SMAC 101 to form lubricious coating 104 on device part 103, which is schematically shown in FIG. 1 as device part 103B. Hydrophilic segments 101A extend into biological media once contacting with blood and provide device part 103 with wet lubricity. Where base polymer 102 is hydrophobic, hydrophobic segment 101B interacts with hydrophobic base polymer 102 to help anchor SMAC 101 to surface 108. Although covalent bonds between base polymer 102 and SMAC 101 are not present, other chemical and physical interactions help entangle hydrophobic segment 101B with base polymer 102 so as to anchor SMAC 101 to surface 108, especially when segment 101B and polymer 102 are selected so as to have similar chemical groups, structures and/or properties.

Device part 103 formed of the blended polymeric material may include any medical part, such as, for example, an intra-aortic balloon or a casing at least partially enclosing the medical device. For example, the medical device may be an implantable lead and device part 103 may include lead insulation tubing. In such a case, a lead insulation material may be used as base polymer 102. Lead insulation materials include, for example, silicone rubber, silicone polyurethane copolymer (SPC), and polyurethane, such as Pellethane 2363 55D. A polystyrene-polyisobutylene-polystyrene triblock copolymer (PSIBS) or other polyisobutylene-based copolymer (e.g., an ABA copolymer in the form X-PIB-X, X being a polymer segment other than PIB) may also be used as base polymer 102. PSIBS may be specifically useful as lead insulation material or to form other medical device parts, since it is highly flexible, and may be more resistant to abrasion and cyclic compression than silicone, and more biostable than Pellethane 55D. PSIBS may be prepared using terminally functional polyisobutylene as an intermediate, and attaching polystyrene segments to each end of the polyisobutylene segment, as should be understood to one skilled in the art. Terminally functional polyisobutylenes are disclosed in U.S. Pat. Nos. 4,316,973 and 4,342,849 to Kennedy, the entire disclosures of which are hereby incorporated by reference. Methods to produce PIB-based copolymers are described in U.S. Pat. No. 4,910,321 to Kennedy et al., the entire disclosure of which is hereby incorporated by reference. For example, a PSIBS copolymer may be constructed as disclosed in U.S. Pat. No. 4,276,394 to Kennedy et al., the entire disclosure of which is hereby incorporated by reference.

In one embodiment of a method disclosed herein, blending step 110 includes melting together SMAC 101 and base polymer 102 in an extruder to produce the blended polymeric material. For example, after base polymer 102 is synthesized, a twin-screw extruder may be used to blend SMAC 101 with base polymer 102. The blended polymeric material may then be pelletized and sent for further processing for forming into device part 103 or may be extruded directly so as to form device part 103.

Alternatively, blending step 110 includes adding SMAC 101 into base polymer 102 during the synthesis of base polymer 102, in which case a twin-screw extruder is not required to mix SMAC 101 and base polymer 102 together. For example, SMAC 101 can be added into a reactant during the synthesis of base polymer. In this case, the synthesized base polymer 102 contains SMAC 101, and a twin-screw extruder is not required to mix SMAC 101 and base polymer 102 together. In step 120, an extrusion method, for example, may be employed to construct device part 103 formed of the blended polymeric material.

Figure 2A:
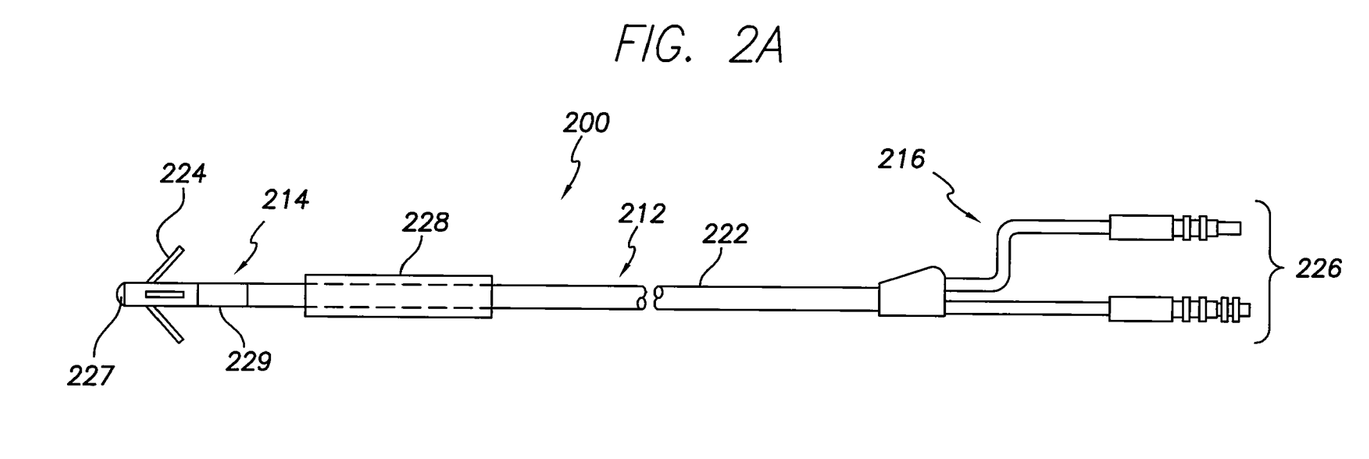
FIG. 2A shows an implantable medical lead in accordance with an embodiment.

An implantable medical device having device part 103 formed of the blended polymeric material will now be described. In one embodiment, the medical device includes a device body and a casing formed of the blended polymeric material which at least partially encloses the device body. The blended polymeric material may include base polymer 101 and any one or combination of the SMACs 101, including the PEO/SI or the PEO/PIB block copolymers further described below. FIG. 2A illustrates an implantable medical device in the form of a body implantable lead 200. Lead 200 includes a device body 212 having a proximal end portion 216 and a distal end portion 214, which includes a tip electrode 227, a shocking electrode 228, and a sensing electrode 229. The proximal end portion 216 includes a bifurcated connector assembly 226 coupling the lead 200 to a pacemaker/defibrillator.

Figure 2B:
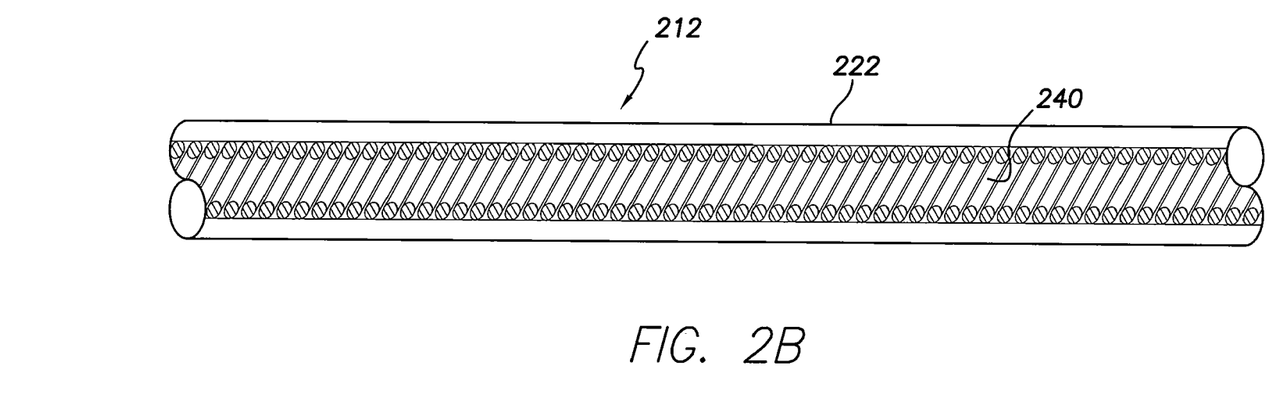
FIG. 2B is an axial cross section of a portion of the lead of FIG. 2A having a lead insulation tubing formed of a blended polymeric material in accordance with another embodiment.

The lead body 212 includes a casing 222 formed of the blended polymeric material. In one embodiment, casing 222 forms an insulative tubing enclosing a coil conductor 240, as illustrated in FIG. 2B. In FIG. 2A, casing 222 extends along substantially the entire length of lead body 212. As noted above, the blended polymeric material forming casing 222 includes an SMAC blended with a base polymer, and therefore a lubricious coating forms on the casing when lead 200 is implanted, which improves biocompatibilities by decreasing protein adsorption, bacteria and cell adhesion, and thrombosis formation. Where casing 222 forms an insulative tubing, the base polymer in the blended polymeric material can be a lead insulation material, such as, for example, silicone rubber, polyurethane, silicone polyurethane copolymer (SPC), PSIBS or other suitable polyisobutylene-based copolymer.

Specific SMACs 101 will now be described. In one embodiment, a specific SMAC 101 includes at least one PEO block and at least one silicone (SI) block wherein the weight average molecular weight ($M_w$) of this particular SMAC is in the range of about 400 to about 50,000. This PEO/SI block copolymer may be in the form of ABA, BAB, AB, for example, and may also be a random multi-block copolymer, represented generally as a copolymer in the form of ABBAA-BABA, as defined above. For this PEO/SI block copolymer, whether in the form of ABA, as illustrated in FIG. 1, or BAB or AB, and so on, each block A includes one or more hydrophilic segments of PEO (101A) and each block B includes one or more hydrophobic segments of SI (101B). For the PEO/SI block copolymer in the form of ABA and BAB, the $M_w$ of the block copolymer may be in the range of about 400 to about 30,000. In one embodiment, the $M_w$ of the PEO/SI block copolymer is in the range of 1,000 to 10,000. In one embodiment where the PEO/SI block copolymer is a random multi-block copolymer described above (ABBAABABA), the $M_w$ of the block copolymer may be in the range of about 5000 to about 50,000. In one embodiment, the $M_w$ of each block A of PEO is in the range of about 150 to about 15,000, and in another embodiment the M, of each block B of SI is in the range of about 200 to about 15,000, whether the PEO/SI block copolymer is the form of ABA, BAB, AB or a random block copolymer. The chain lengths of segment(s) in a block A (or in a block B) may be the same or different within the same block, and the same or different with respect to the segment(s) of another block A (or another block B) if the PEO/SI block copolymer contains more than one block A (or more than one block B).

In one embodiment, when multiple segments of PEO in a block A and/or multiple segments of SI in a block B are present, the segments within the block are connected together using isocyanate chemistry. Isocyanate chemistry may also be used to couple a block A and a block B together. In one embodiment, the PEO/SI block copolymer in the form of ABA may contain one SI segment or multiple SI segments connected together by a linkage DI. As shall be further described below, DI represents the linkage which is produced by reacting each of the isocyanate groups of a diisocyanate with a reactive/functional group from a PEO or SI segment. Each functional group may be an hydroxyl or amine group, for example. In such a case, DI may include a urethane or urea linkage having two urethane or urea functional groups between coupled segments or blocks.

As is well known in the art, a diisocyanate can be employed as a linking or coupling agent via the following chemistry shown in Scheme 1.

For example, in the case of cyclohexyl diisocyanate, Y would be

For a PEO/SI block copolymer in the form of ABA, a block B may include n SI segments connected together by DI. In such a case, n moles of di-reactive group terminated silicone (diSI) molecules may be reacted with n+1 moles of a diisocyanate, where n is an integer greater than zero, thereby forming n segments connected together. The combined segments are terminated on the ends by an isocyanate group to form an isocyanate-terminated prepolymer to later allow coupling of block B to blocks A, as further described below. The diisocyanate may include, for example, methylene bis-(4-phenyl isocyanate) (MDI), hexamethylene diisocyanate (HMDI), methylene bis (p-cyclohexyl isocyanate) (H12MDI), 3,3-bi-toluene diisocyanate (TODI), cyclohexyl diisocyanate (CHDI), or toluene diisocyanate (TDI). For the DI connecting SI segments together, the DI is a product of reacting the diisocyanate with the reactive groups of diSI. DI will include a urethane or urea linkage when the reactive groups of diSI are hydroxyl or amine groups, respectively. The resulting urethane or urea linkage between coupled SI segments may include two urethane or urea functional groups (with an organic residue in between) resulting from reacting the two isocyanate groups of the diisocyanate. DI may also be the linkage coupling SI and PEO segments together, when isocyanate groups are used as a coupling agent, as further described below. In such an instance, the PEO/SI block copolymer is represented by the formula PEO-DI-(SI-DI)$_n$-PEO. Hence, where n is greater than one, a PEO/SI block copolymer in the form of ABA includes multiple SI segments linked together to form block B.

Exemplary methods for making the PEO/SI block copolymer of various forms will now be described. For synthesis of PEO-DI-(SI-DI)$_n$-PEO, a two-stage method may be employed. Firstly, as described above, n+1 moles of a diisocyanate is reacted with n moles diSI to obtain an isocyanate-terminated prepolymer (i.e., SI terminated on each end with an isocyanate group). Secondly, two moles of mono-functional group terminated polyethylene oxide (mPEO) are reacted with one mole of the isocyanate-terminated prepolymer. An exemplary diSI may be a SI molecule terminated on each end by a reactive group such as a hydroxyl or an amine group. An exemplary mPEO may be a PEO molecule terminated on one end by a functional group such as a hydroxyl or amine group. In such a case, DI may be a urethane or urea linkage having two urethane or urea functional groups between coupled blocks of PEO and SI. The other end of the PEO molecule may be terminated by a suitable alkoxy group, such as methoxy or ethoxy, for example. Accordingly, a specific mPEO may be a monomethoxy, monohydroxyl-terminated PEO.

A similar two-stage synthesis method may be used for making the PEO/SI block copolymer in the form BAB represented by the formula SI-DI-(PEO-DI)$_n$-SI, wherein n is an integer greater than zero, such that block A has one or more segments of PEO. Accordingly, the block A may be one PEO segment or multiple PEO segments connected together by DI. Using the two-stage method described above, SI-DI-(PEO-DI)$_n$-SI is formed by firstly reacting n+1 moles of a diisocyanate with n moles of di-reactive PEO (diPEO) to obtain an isocyanate-terminated prepolymer, and secondly reacting two moles of mono-functional group terminated SI (mSI) (e.g., monomethoxy, monohydroxy-terminated SI) with one mole of the isocyanate-terminated prepolymer. The diPEO is terminated on each end by a reactive group such as a hydroxyl or amine group. The mSI is terminated by a functional group such as a hydroxyl or amine group on one end of the mSI molecule. For mPEO, mSI, diPEO, and diSI, it should be understood that other reactive groups can also be used to react with isocyanates to prepare the PEO/SI block copolymers.

The exemplary two-stage method discussed above may also be used for making the PEO/SI block copolymer in the form AB represented by the formula PEO-DI-SI. In this case, one mole of diisocyanate is reacted with one mole of mSI to obtain a monoisocyanate-terminated prepolymer, and one mole of mPEO is reacted with one mole of the monoisocyanate-terminated prepolymer.

For synthesis of a random multi-block copolymer represented by the formula PEO-DI-SI-DI-SI-DI-PEO-DI-PEO-DI-SI-DI-PEO-DI-SI-DI-PEO, the exemplary two-stage method includes (1) reacting n+1 moles of diisocyanate with m moles of diSI and n-m moles of diPEO to obtain a multi-block isocyanate-terminated prepolymer, wherein n and m are integers greater than zero, and (2) reacting two moles of mPEO with one mole of the isocyanate-terminated prepolymer.

Another specific SMAC 101 presented herein includes at least one PEO block and at least one polyisobutylene (PIB) block. This PEO/PIB block copolymer may be in the form of ABA, BAB, AB, for example, and may also be a random multi-block copolymer, represented generally as a copolymer in the form of ABBAABABA, as defined above. For this PEO/PIB block copolymer, whether in the form of ABA, as illustrated in FIG. 1, or BAB or AB, and so on, each block A includes one or more hydrophilic segments of PEO (101A) and each block B includes one or more hydrophobic segments of PIB (101B). For the PEO/PIB block copolymer in the form of ABA and BAB, the $M_w$ of the block copolymer may be in the range of about 400 to about 60,000. In one embodiment where the PEO/PIB block copolymer is a random multi-block copolymer described above, the $M_w$ of the PEO/PIB block copolymer may be in the range of about 5000 to about 60,000. In one embodiment, the $M_w$ of each block A of PEO is in the range of about 150 to about 20,000, and in another embodiment the $M_w$ of each block B of PIB is in the range of about 200 to about 30,000, whether the PEO/PIB block copolymer is the form of ABA, BAB, AB or a random block copolymer. A single segment of PIB of block B may have $M_w$ in the range of about 200 to about 20,000. The chain lengths of segment(s) in a block A (or in a block B) may be the same or different within the same block, and the same or different with respect to the segment(s) of another block A (or another block B) if the PEO/PIB block copolymer contains more than one block A (or more than one block B).

In one embodiment, when multiple segments of PEO in a block A and/or multiple segments of PIB in a block B are present, DI is the linkage between the segments of a block, as well as between the blocks A and/or B. Such a final product may be obtained using a two-stage synthesis method similar to that described above for the PEO/SI block copolymers. For a PEO/PIB block copolymer in the form of ABA, a block B may include n PIB segments connected together by DI. In such a case, n moles of di-reactive group terminated polyisobutylene (diPIB) molecules may be reacted with n+1 moles of a diisocyanate, where n is an integer greater than zero, thereby forming n PIB segments connected together. The DI is a product of reacting the diisocyanate with the reactive groups of diPIB. DI may be a urethane or urea linkage when the reactive groups of diPIB are hydroxyl or amine groups, respectively. The resulting urethane or urea linkage between coupled PIB segments may include two urethane or urea functional groups resulting from reacting the two isocyanate groups of the diisocyanate. The combined segments are terminated on the ends by an isocyanate group to form an isocyanate-terminated prepolymer to later allow coupling of block B to blocks A, as further described below. Thus, DI may also be the linkage coupling PIB and PEO segments together, when isocyanate groups are used as a coupling agent, as further described below. In such an instance, the PEO/PIB block copolymer is represented by the formula PEO-DI-(PIB-DI)$_n$-PEO. Hence, where n is greater than one, a PEO/PIB block copolymer in the form of ABA includes multiple PIB segments linked together to form block B.

For synthesis of PEO-DI-(PIB-DI)$_n$-PEO, a two-stage method may be employed. Firstly, as described above, n+1 moles of a diisocyanate is reacted with n moles diPIB to obtain an isocyanate-terminated prepolymer (i.e., PIB terminated on each end with an isocyanate group). Secondly, two moles of mono-functional group terminated polyethylene oxide (mPEO) are reacted with one mole of the isocyanate-terminated prepolymer. An exemplary diPIB may be a PIB molecule terminated on each end by a reactive group such as a hydroxyl or an amine group. An exemplary mPEO may be a PEO molecule terminated on one end by a functional group such as a hydroxyl or amine group. In such a case, DI may be a urethane or urea linkage having two urethane or urea functional groups between coupled blocks of PEO and PIB. The other end of the PEO molecule may be terminated by a suitable alkoxy group, such as methoxy or ethoxy, for example. Accordingly, a specific mPEO may be a monomethoxy, monohydroxyl-terminated PEO.

A similar synthesis two-stage method may be used for making the PEO/PIB block copolymer in the form BAB represented by the formula PIB-DI-(PEO-DI)$_n$-PIB, wherein n is an integer greater than zero, such that block A has one or more segments of PEO. Accordingly, the block A may be one PEO segment or multiple PEO segments connected together by DI. Using the two-stage method described above, PIB-DI-(PEO-DI)$_n$-PIB is formed by firstly reacting n+1 moles of a diisocyanate with n moles of di-reactive PEO (diPEO) to obtain an isocyanate-terminated prepolymer, and secondly reacting two moles of mono-functional group terminated PIB (mPIB) (e.g., monomethoxy, monohydroxy-terminated PIB) with one mole of the isocyanate-terminated prepolymer. The diPEO is terminated on each end by a reactive group such as a hydroxyl or amine group. The mPIB is terminated by a functional group such as a hydroxyl or amine group on one end of the mPIB molecule. For mPEO, mPIB, diPEO, and diPIB, it should be understood that other reactive groups can also be used to react with isocyanates to prepare the PEO/PIB block copolymers.

The exemplary two-stage method discussed above may also be used for making the PEO/PIB block copolymer in the form AB represented by the formula PEO-DI-PIB. In this case, one mole of diisocyanate is reacted with one mole of mPIB to obtain a monoisocyanate-terminated prepolymer, and one mole of mPEO is reacted with one mole of the monoisocyanate-terminated prepolymer.

For synthesis of a random multi-block copolymer represented by the formula PEO-DI-PIB-DI-PIB-DI-PEO-DI-PEO-DI-PIB-DI-PEO-DI-PIB-DI-PEO, the exemplary two-stage method includes (1) reacting n+1 moles of diisocyanate with m moles of diPIB and n-m moles of diPEO to obtain a multi-block isocyanate-terminated prepolymer, wherein n and m are integers greater than zero, and (2) reacting two moles of mPEO with one mole of the isocyanate-terminated prepolymer.

SMACs are particularly advantageous when hydrophobic block B of SMAC 101 has a chemical structure similar to base polymer 102, because interactions between the hydrophobic block B and a hydrophobic matrix of base polymer 102 help to anchor lubricious coating 104 to surface 108. The interactions may involve chain entanglements and various other physical interactions. For example, with reference to the schematic of FIG. 1, where a PEO/PIB block copolymer, such as PEO-PIB-PEO, is used as SMAC 101, and PSIBS, or other polyisobutylene-based copolymer, is used as base polymer 102, strong interactions between hydrophobic base polymer 102 having a PIB block and the hydrophobic PIB segment(s) (101B) of the PEO/PIB block copolymer help to anchor lubricious coating 104 to surface 108. Where a PEO/SI block copolymer, such as PEO-SI-PEO, is used as SMAC 101, and silicone rubber or a silicone polyurethane copolymer, for example, is used as base polymer 102, strong interactions between a silicone matrix of base polymer 102 and silicone block (101B) of the PEO/SI block copolymer help to anchor lubricious coating 104 to surface 108.

The PEO/SI or PEO/PIB block copolymers described herein are SMACs which may be employed in the methods outlined above for providing a lubricious coating on a medical device. For example, a PEO/SI or PEO/PIB block copolymer may be blended with the base polymer as an additive, either by adding to a reactant during synthesis of base polymer 102 or by melting the block copolymer and the base polymer together in an extruder, to produce the blended polymeric material used to form device part 103 of a medical device, such as casing 222 in FIGS. 2A and 2B described above. When the device is implanted, the block copolymer migrates to an outer surface of the device part formed of the blended polymeric material since the block copolymer is surface active. The PEO/SI or PEO/PIB block copolymers can be also used for other applications, both in and out of the medical field. Moreover, other methods can be employed using the PEO/SI or PEO/PIB block copolymers to prepare lubricious coatings of substrates. For example solution casting, dip-coating and adsorption techniques further described below may be employed.

An example solution-casting method to obtain device part 103 formed of the blended polymeric material via solution-casting may include the steps of mixing the PEO/SI or PEO/PIB block copolymers with base polymer 102 in solution to produce a solution mixture, casting the solution mixture, and evaporating the solvent. For example, dimethyl formamide (DMF) or other solvent may be used as a cosolvent for the block copolymer and the base polymer. The base polymer may be dissolved in DMF at a concentration in a range of 2-25%, such as 5%. The block copolymer may be dissolved in the polymer solution at a concentration in a range between 0.2% and 40% by weight of base polymer content. Alternatively, solutions of the block copolymers and the base polymer may be prepared separately and then mixed. To prepare a film of the blended polymeric material, for example, the mixed polymer solution is cast onto clean casting dishes and the cast films are dried in a ventilation oven at 60 degrees for 24 hours and then in a vacuum oven at 60 degrees for 24 hours to remove the solvent. A crosslinking agent may be added to the solution mixture to permanently prevent the block copolymer from escaping surface 108 of device part 103. By "permanently prevent" is meant that the crosslinking substantially entraps the PEO/SI (or PEO/PIB) block copolymer in base polymer 102 so that little or none of the block copolymer leaches out into contacting bodily fluids. An example procedure for crosslinking is described in *Platelet adhesion onto segmented polyurethane film surfaces modified by addition and crosslinking of PEO-containing block copolymers*, J. H. Lee, et al., Biomaterials 21:683-691 (2000), incorporated herein by reference in its entirety.

An implantable medical device such as lead 200 described above with reference to FIGS. 2A and 2B may include a device body 212 at least partially formed of a polymeric material including a base polymer and selected block copolymers of one or more SMACs. For example, the selected block copolymers may include any one or combination of the PEO/SI block copolymers described above, or in another embodiment, any one or combination of PEO/PIB block copolymers described above. In one embodiment, the selected block copolymer is a PEO/SI block copolymer described herein, and in another embodiment, the selected block copolymer is a PEO/PIB block copolymer represented by the formula PEO-DI-(PIB-DI)$_n$-PEO, which may be made using the two-stage method described above. In another embodiment, the selected block copolymers are one or more PEO/SI block copolymers used together with one or more other SMACs 101. In another embodiment, the selected block copolymers are one or more PEO/PIB block copolymers together with one or more other SMACs 101.

In one embodiment, the implantable medical device is a lead, the base polymer is a lead insulation material, such as silicone, silicone polyurethane copolymer, polyurethane, or PSIBS or other polyisobutylene-based copolymer suitable for lead insulation material, and the device part formed of the polymeric material is lead insulation tubing, such as casing 222 in FIGS. 2A and 2B or a later-described device body 312 illustrated in FIG. 3. The selected block copolymers form a lubricous coating on lead insulation tubing 222 or 312 when lead 200 is implanted.

Figure 3:
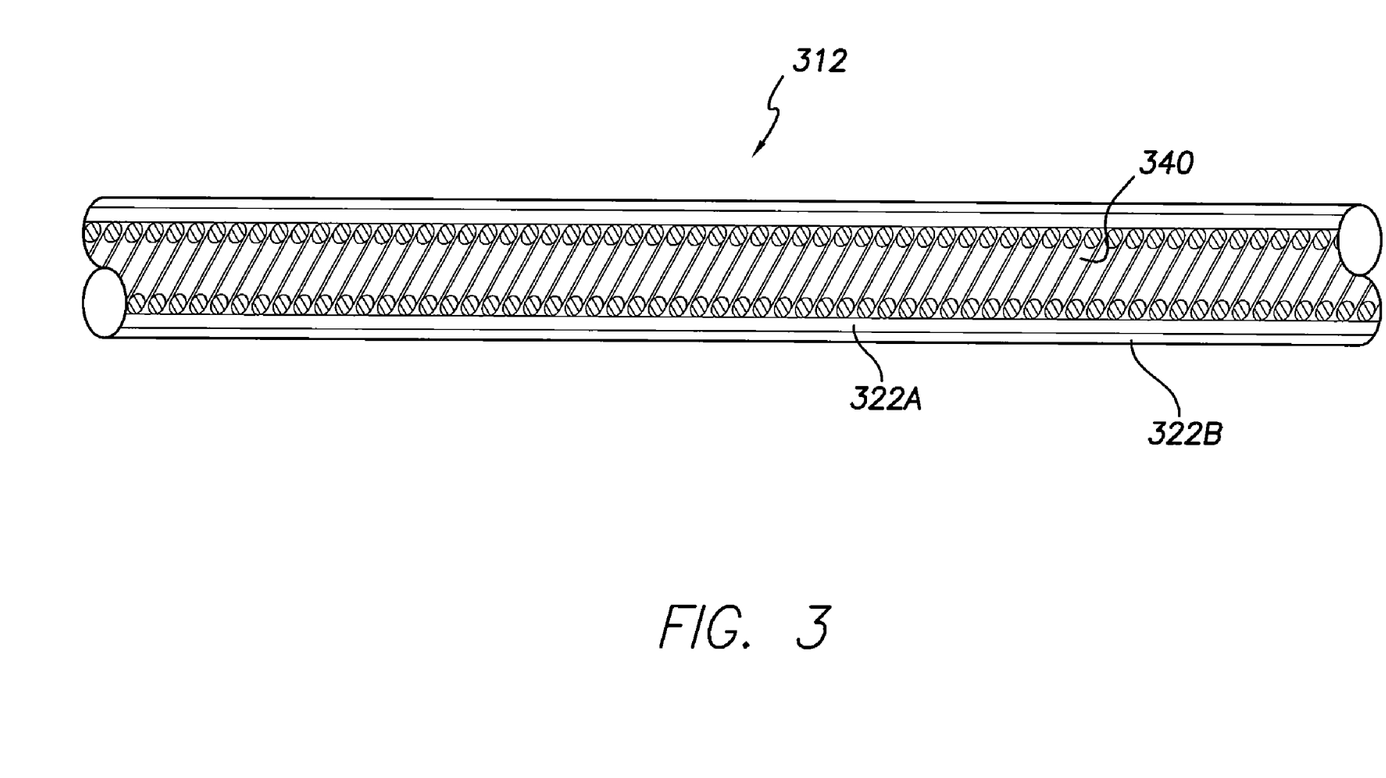
FIG. 3 is an axial cross section of a portion of the lead of FIG. 2A having a lead body formed of an inner base polymer layer and an outer SMAC layer in accordance with another embodiment.

In another embodiment, illustrated in FIG. 3 as an axial cross-section of a portion of the lead of FIG. 2A, the polymeric material at least partially forms a device body 312 which includes an inner layer 322a formed of the base polymer coated by an outer layer 322b formed of the selected block copolymers. In FIG. 3, device body 312 including layers 322a and 322b coaxially surrounds a coil conductor 340. In one embodiment, outer layer 322b may be deposited on inner layer 322a using a coating method, such as dip-coating or adsorption methods, or other methods of forming outer layer 322b and affixing to inner layer 322a. For example, to obtain outer layer 322b deposited on inner layer 322a by dip-coating, inner layer 322a is immersed in a solution mixture of the selected block copolymers and a solvent, which may be water or an organic chemical, and the solvent is evaporated. An adsorption method may include immersing inner layer 322a into an aqueous solution of the selected block copolymers and allowing the selected block copolymers to be adsorbed on the surface of inner layer 322a so as to form outer layer 322b. Adsorption occurs through the strong hydrophobic interactions between the hydrophobic segment(s) of the selected block copolymers of outer layer 322b and a hydrophobic matrix included in the base polymer of inner layer 322a. For example, in one embodiment, outer layer 322b is formed of a PEO/PIB block copolymer, and the base polymer of inner layer 322a includes PSIBS or other poly-isobutylene-based copolymer. The PIB segment(s) of the PEO/PIB block copolymer of outer layer 322b interact with the PIB segment of the base polymer due to their similar chemical structures. These strong interactions anchor the PEO/PIB block copolymer of outer layer 322b to base polymer of inner layer 322a. In another embodiment, outer layer 322b is formed of a PEO/SI block copolymer, and the base polymer of inner layer 322a includes silicone or SPC. The SI segment(s) of the PEO/SI block copolymer of outer layer 322b interact with the silicone matrix of the base polymer due to their similar chemical structures. These strong interactions anchor the PEO/SI block copolymers of outer layer 322b to base polymer of inner layer 322a.

Example embodiments of the methods, systems, and components of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments, but should be defined only in accordance with the following claims and their equivalents.

What is claimed is:

1. An implantable medical device, comprising a device body at least partially formed of a polymeric material including a base polymer and a block copolymer, the block copolymer having at least one polyethylene oxide block (PEO) and at least one silicone block, wherein the weight average molecular weight of the block copolymer is in the range of about 400 to about 50,000, wherein the base polymer material is one of a silicone rubber or a silicone polyurethane copolymer and the block copolymer is the form of ABA, BAB, AB, or a random multi-block copolymer represented generally in the form of ABBAABABA, and wherein the block A is PEO and the block B is silicone.

2. The implantable medical device of claim 1, wherein the polymeric material is an inner layer coated by an outer layer, the inner layer being formed of the base polymer and the outer layer being formed of the block copolymer.

3. An implantable medical device, comprising a device body at least partially formed of a polymeric material including a base polymer and a block copolymer, the block copolymer having at least one polyethylene oxide block (PEO) and at least one silicone block, wherein the weight average molecular weight of the block copolymer is in the range of about 400 to about 50,000, wherein the block copolymer is blended as an additive into the base polymer, the block copolymer migrating to an outer surface of the device body formed of the polymeric material when the device is implanted so as to provide the device with wet lubricity.

* * * * *